United States Patent [19]
Isaza et al.

[11] Patent Number: 5,813,399
[45] Date of Patent: Sep. 29, 1998

[54] SYSTEM AND METHOD FOR CLOSED LOOP AIRWAY PRESSURE CONTROL DURING THE INSPIRATORY CYCLE OF A BREATH IN A PATIENT VENTILATOR USING THE EXHALATION VALVE AS A MICROCOMPUTER-CONTROLLED RELIEF VALVE

[75] Inventors: Fernando J. Isaza, San Marcos; Stanley Y. Wong, Oceanside, both of Calif.

[73] Assignee: Puritan Bennett Corporation, Carlsbad, Calif.

[21] Appl. No.: 782,563

[22] Filed: Jan. 10, 1997

Related U.S. Application Data

[63] Continuation of Ser. No. 366,293, Dec. 28, 1994, abandoned, which is a continuation-in-part of Ser. No. 33,259, Mar. 16, 1993, abandoned.

[51] Int. Cl.⁶ .......................... A61M 16/00; A62B 7/00; A62B 9/02; F16K 31/02
[52] U.S. Cl. ................... 128/204.21; 128/205.24
[58] Field of Search .................. 128/204.18, 204.21, 128/204.22, 204.23, 204.26, 205.24

[56] References Cited

U.S. PATENT DOCUMENTS

| | | |
|---|---|---|
| 4,036,221 | 7/1977 | Hillsman et al. . |
| 4,454,893 | 6/1984 | Orchard . |
| 4,527,557 | 7/1985 | DeVries et al. . |
| 4,611,591 | 9/1986 | Inui et al. . |
| 4,699,137 | 10/1987 | Schroeder . |
| 4,838,257 | 6/1989 | Hatch . |
| 4,928,684 | 5/1990 | Breitenfelder et al. . |
| 4,941,469 | 7/1990 | Adahan . |
| 5,020,532 | 6/1991 | Mahoney et al. . |
| 5,044,362 | 9/1991 | Younes . |
| 5,063,925 | 11/1991 | Frank et al. . |
| 5,065,746 | 11/1991 | Steen . |
| 5,072,729 | 12/1991 | DeVries . |
| 5,097,424 | 3/1992 | Ginevri et al. . |
| 5,107,830 | 4/1992 | Younes . |
| 5,129,390 | 7/1992 | Chopin et al. . |
| 5,245,995 | 9/1993 | Sullivan et al. . |

FOREIGN PATENT DOCUMENTS

| | | |
|---|---|---|
| 0 402 951 | 12/1990 | European Pat. Off. . |
| 8910769 | 11/1989 | WIPO ............................. 128/204.23 |

*Primary Examiner*—Kimberly L. Asher
*Attorney, Agent, or Firm*—Fulwider Patton Lee & Utecht, LLP

[57] ABSTRACT

The method and system for controlling airway pressure in a ventilator during the inspiratory cycle involves controlling the flow of breathing gas through a flow supply valve venting the breathing gas at a desired rate of outflow through a relief valve to achieve the desired airway pressure. Measurements of the rates of actual supply flow, the actual outflow through the exhalation/relief valve, and the pressure in the airway are compared with desired values for determination the amount of error for feedback control of the ventilator system.

15 Claims, 5 Drawing Sheets

IF $P_{aw} = P_2$, then $force_{open} < force_{close}$

IF $force_{open} = force_{close}$ then $P_{aw} = P_2 \times \left(\dfrac{area_{D2}}{area_{aw}}\right)$ $$\dfrac{P_{aw}}{P_2} = \dfrac{area_{D2}}{area_{aw}} = \dfrac{area}{ratio}$$

$D_2 > D_{aw}$ therefore $area_{aw} < area_{D2}$ $force_{open} = P_{aw} \times area_{aw}$ $force_{close} = P_2 \times area_{D2}$ PRESSURE CONTROLLED INSPIRATION PHASE USING A PRIOR ART CONTROLLER FOR A DESIRED PRESSURE OF 30 cm $H_2O$.

PRESSURE CONTROLLED INSPIRATION PHASE USING THE CONTROL SYSTEM OF THE INVENTION FOR A DESIRED PRESSURE OF 30 cm $H_2O$.

SYSTEM AND METHOD FOR CLOSED LOOP AIRWAY PRESSURE CONTROL DURING THE INSPIRATORY CYCLE OF A BREATH IN A PATIENT VENTILATOR USING THE EXHALATION VALVE AS A MICROCOMPUTER-CONTROLLED RELIEF VALVE

RELATED APPLICATIONS

This application is a continuation of application Ser. No. 08/366,293, filed Dec. 28, 1994, now abandoned, which is a CIP of Ser. No. 08/033,259, filed Mar. 16, 1993, which is now abandoned.

BACKGROUND OF THE INVENTION

1. Field of the Invention

This invention relates generally to breathing ventilators, and more particularly relates to a system and method for controlling patient airway pressure during the inspiratory cycle of a breath by control of a flow delivery valve and a relief valve in combination to achieve a desired pressure level.

2. Description of Related Art

Medical ventilators are designed to assist a patient in breathing when the patient is somehow unable to adequately breath on his own. In some form of ventilator systems, the patient is provided with ventilation support in the form of pressure assistance after the patient has began his inspiratory effort. With such a system, it is desirable to immediately increase the pressure after a breath is initiated in order to reach a target pressure input by the care provider. This rise in pressure causes flow to be initiated in the patient airway which supplies breathing gas to the patient's lungs. Conventional pressure controlled ventilator systems control the flow of gas to the patient by use of a pressure controller, a flow controller and flow valve in the inlet side of the airway, terminating the flow when the target pressure is reached.

However, such a control strategy often results in over pressurization of the patient, with the pressure overshooting the target pressure by a greater or lesser amount depending on the physiology of the patient and the construction of the airway. Often, the overshoot is sustained, thus over pressurizing the patient's lungs for the entire inspiration cycle of the breath. When this occurs, the possibility exists that the patient will be harmed by the higher than desirable pressure in the lungs. For instance, if the patient has recently had thoracic or abdominal surgery, the possibility exists that such over pressures could rupture sutures or blood vessels recently repaired in the surgery. Similarly, a very frail or infirm patient such as one with asthma or emphysema could be harmed if the breath pressure is in excess of that desired.

For these reasons, it would be desirable if the delivery of breaths in a pressure controlled ventilator could be controlled to reduce short term pressure spikes due to increases in flow and to eliminate long term overshoot or long term over-pressurization in the patient airway. It would be particularly advantageous if the control of such overshoots could be accomplished without significant changes to the basic configuration and utilized existing components. The present invention accomplishes these goals.

SUMMARY OF THE INVENTION

Briefly, and in general terms, the present invention provides a system and method for the control of patient ventilator airway pressure during the inspiration cycle of a breath by controlling both the flow delivery supply valve and a relief valve, both valves being in communication with the patient airway. Prior to the beginning of an inspiratory cycle of a breath, the flow control valve is controlled to supply a flow of breathing gas to the patient and through a relief valve in the exhalation flow path at a rate that biases the exhalation valve into the "flat" portion of the valve's pressure vs. flow characteristics and thus accomplishes reduction of pressure overshoot even though flow may still increase before gas delivery is over. Upon commencement of the inspiratory cycle of a breath, the flow control valve is controlled to supply breathing gas at a rate required to achieve a desired airway pressure level and the relief valve is opened in response to signals from a relief valve flow controller based on a desired relief valve flow rate and the measured exhalation flow rate. By use of the invention, improved control of the pressure in the patient airway is obtained, particularly with regard to controlling short term pressure overshoot and sustained over-pressurization during the inspiratory cycle.

A current problem encountered during the inspiratory cycle of patient respirators is the control of overshoot of patient airway pressure during the inspiration cycle for pressure controlled type of ventilation. When the cycle is primarily controlled by the standard pressure and flow controllers, the patient is likely to experience an overshoot in the airway pressure as the controllers command the flow valve opening to rapidly supply breathing gas to the patient during the initial phases of the inspiration. Such an overpressure is often unavoidable if rapid filling of the patient airway is required and only control of the flow valve is available. Thus, it is highly desirable to provide more accurate control of patient airway pressure during the inspiration cycle of the breathing cycle, since over-pressurization of the patient's lungs has a number of undesirable effects.

The present invention utilizes conventional delivery side pressure and flow controllers as well as an actively controlled flow level through an actively controlled relief valve in combination with a ventilator breathing gas supply system to control, via a flow control valve and patient tubing system, the supply of breathing gas to a patient. In order to more accurately control the pressure in the patient airway, a relief valve is provided in the exhalation flow path to allow for the venting of breathing gas both at a predetermined flow target and in response to control inputs during inspiration. The control inputs to the relief valve are derived from a signal representing the difference between a desired level of relief flow and the actual relief valve flow. Using the method and apparatus of the invention, the pressure in the patient airway can be controlled to minimize overshoot, even if very aggressive initial flow rates are used to insure rapid filling of the lungs during the first stages of the inspiration cycle.

In a presently preferred embodiment of the invention, the desired patient airway pressure is summed with the measured patient airway pressure to create an error signal to be used as an input to a pressure controller. The pressure controller outputs a flow control signal representing the desired flow to achieve the desired pressure. The flow control signal is summed with the output of the flow valve to provide an error signal used to drive the flow valve controller. A relief valve, which is preferably an adjustable, actively controlled valve, is connected to the patient airway and driven by a command signal derived from a signal representing a relief flow error signal. The relief error signal is based on the difference between the measured relief valve flow and the desired relief valve flow, which is established based on a number of factors related to system and medical parameters. For example, patients are often medicated by nebulizers and the like, which results in the presence of unabsorbed medicants in the exhaled breathing gas. In such a case it may be desirable to limit the relief valve flow to a relatively low level such as 1 Liter/minute in order to limit exposure of others to the patient's medication. In general, it is desirable to limit the relief valve flow after the overshoot is over, to limit the usage of gasses by the respirator. In a presently preferred embodiment, the relief valve may advantageously be an exhalation valve of the force balance variety well known in the art. Such valves may be controlled by electrical, pneumatic or mechanical inputs.

From the above, it can be seen that the present invention provides an improved method and apparatus for the control of patient airway pressure during the inspiratory cycle of the patient breath on a ventilator by actively controlling both the flow control valve and a relief valve, which can be an exhalation valve, thereby providing both a rapid rise time of pressure and flow and a reduction in overshoot of airway pressure past a desired target pressure. Other aspects and advantages of the invention will be apparent from the following detailed description and the accompanying drawings, which illustrate, by way of example, the features of the invention.

DETAILED DESCRIPTION OF PREFERRED EMBODIMENTS

Pressure controlled ventilation systems provide pressure supported flow of breathing gas to a patient after the ventilator has sensed the initiation of a breath by the patient. However, if the flow of gas is not precisely controlled, the patient airway, and thus the patient's lungs, can be over pressurized by a pressure rise above the target level. In such an event, the patient can experience discomfort or possible harm from the effect of the higher pressure on the respiratory system.

Figure 1:
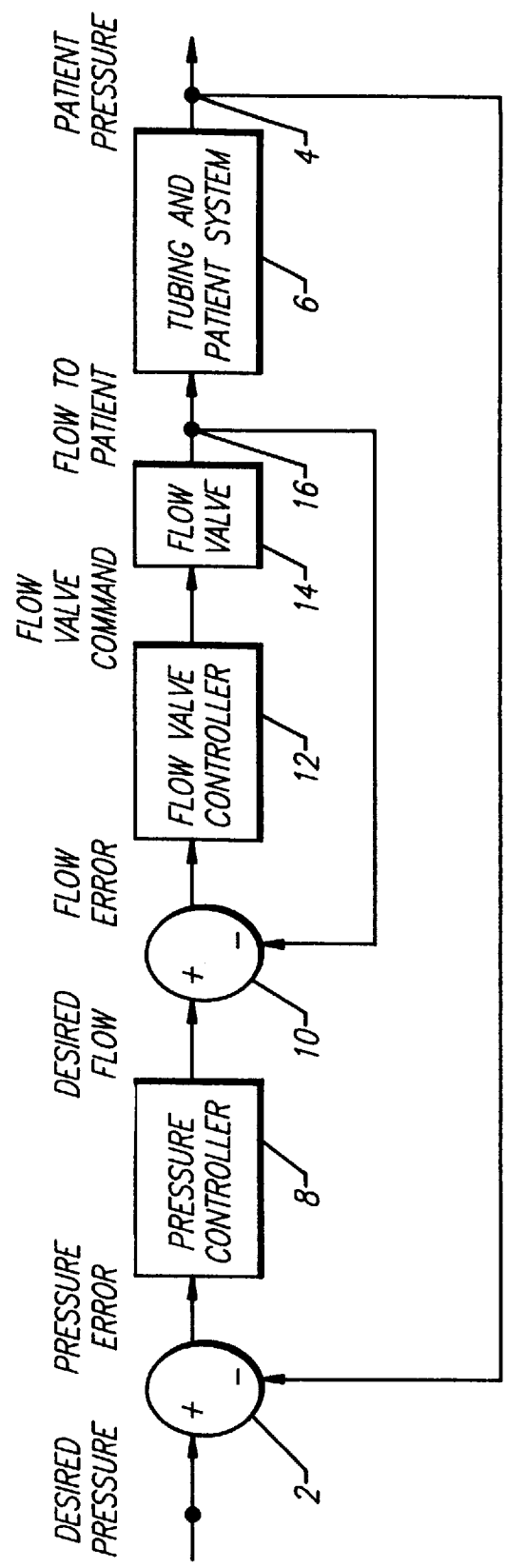
FIG. 1 is a schematic diagram of a prior art ventilator pressure controlled inspiratory breath control system.

A prior art pressure controlled ventilator control system illustrated in FIG. 1 includes a means to input a desired pressure to an error summing means 2 which also receives an input from a pressure sensor 4 measuring patient pressure in the patient airway system 6. The difference between measured pressure and desired pressure is an error signal which is used as an input to the pressure controller 8 which generates a signal representing desired flow rate. The desired flow rate is summed with the signal from flow sensor 16 by summing means 10 to create a flow error signal used as an input to flow valve controller 12, which generates a flow valve command to drive flow valve 14. Flow valve 14 controls flow to the patient airway and tubing system 6.

Figure 4A:
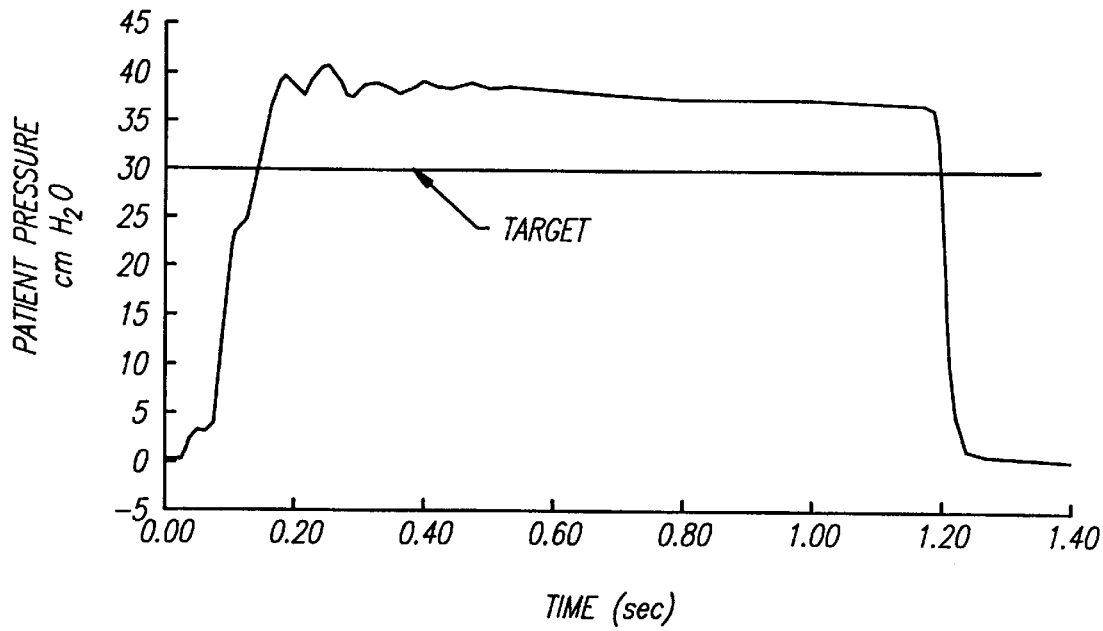
FIGS. 4(a) and 4(b) illustrate a pressure controlled inspiration phase using the prior art controllers.
Figure 4B:
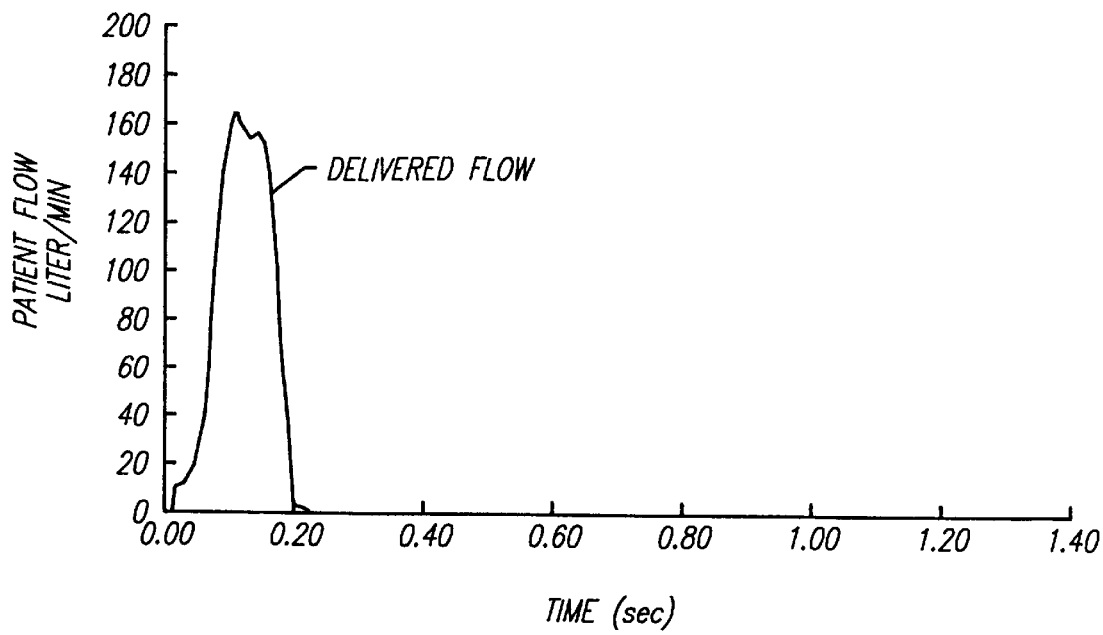

The use of the invention in combination with prior art ventilators has demonstrated substantial improvements in performance. FIGS. 4(a) and 4(b) illustrate the pressure and flow time histories for a ventilator inspiration phase utilizing prior art controllers. More specifically, FIG. 4(a) illustrates the patient pressure in cm of $H_2O$ at the patient wye for a commanded and desired pressure of 30 cm $H_2O$. As will be noted from this trace of pressure produced by prior art controllers, the patient airway pressure persists at a pressure on the order of 7 cm of $H_2O$ above the desired pressure for a substantial portion of the breath after the beginning of inspiration. While this overshoot can be somewhat moderated if a slower initial inspiration rate is used, such a strategy results in less rapid filling of the lungs during the inspiration, and thus inferior ventilation. As illustrated in FIG. 4(b), when compared with FIG. 4(a), the patient overpressure persists long after the delivery of gas is completed, an undesirable result of the use of prior art controllers.

Using such a system, the reservoir represented by the patient airway and the patient's lungs is filled rapidly after initiation of a breath with pressure support. Ideally, gas flow should be cut off as soon as a target pressure is reached; however, the dynamic response of prior art controllers and gas delivery systems often results in an overshoot of pressure resulting in over pressurization of the patient.

Figure 2:
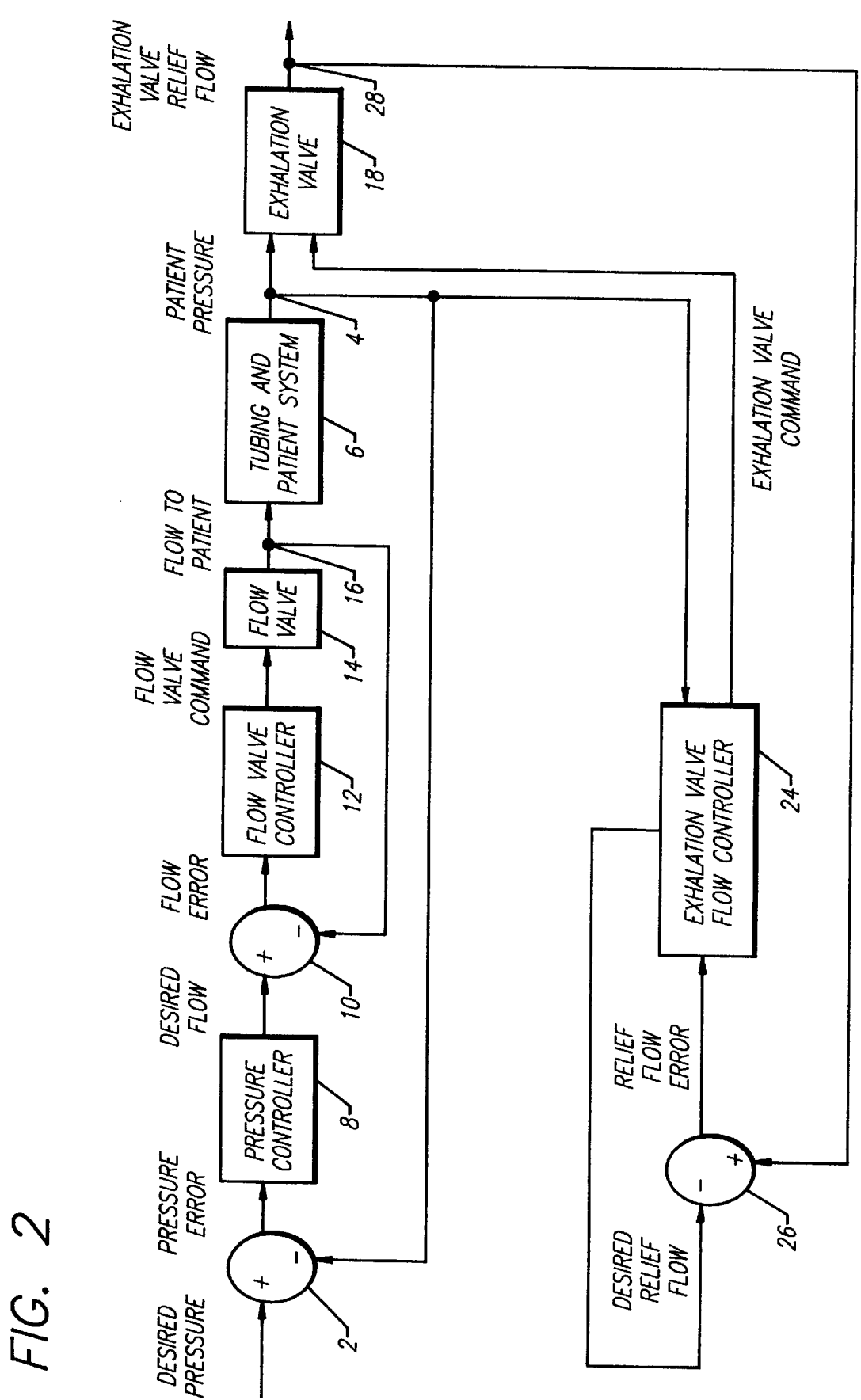
FIG. 2 is schematic diagram of the pressure controlled ventilator inspiratory breath control system of the invention.

The present invention is embodied in a system and method for actively controlling both the inspiratory flow and pressure and a relief valve in the patient circuit system to prevent significant sustained overshoot of pressure beyond the target set by the care provider. As illustrated in FIG. 2, the present invention utilizes a pressure controlled ventilation system of the type illustrated in FIG. 1, along with active control of a relief valve, which could be the exhalation valve, to control the airway pressure. More specifically, summer 2 outputs an error signal which is used as an input to the pressure controller 8 on the basis of an input desired pressure and the measured airway pressure from pressure sensor 4. Pressure controller 8 outputs a desired flow rate which is summed by summing means 10 with the flow rate measured by flow sensor 16. The output of summing means 10 is used to drive flow valve controller 12 and thus flow valve 14 to provide a rate of flow to the patient through patient airway 6. The invention also generates inputs to the flow controller that are a function of patient pressure and also a function of the phase of the inspiratory cycle of the patient. These signals are generated within the exhalation valve flow controller. These signals are then provided as outputs of exhalation valve flow controller 24, which is in turn driven by the output of summing means 26. Summing means 26 outputs a relief flow error signal input to exhalation valve flow controller derived from a desired relief flow and the exhalation valve relief flow measured by exhalation valve relief flow sensor 28.

By the method and apparatus of the invention, overshoot of pressure in the patient airway is actively controlled by providing a predetermined preinspiratory flow target rate of breathing gas through the relief valve in the exhalation flow path, and by actively controlling the exhalation valve on the basis of sensed flow and sensed pressure. The predetermined flow target rate through the relief valve in the exhalation flow path is calculated in the exhalation valve flow controller and is a function of the actual pressure level (4) present at the exhalation valve and the different inspiration stages in a breath (e.g. rise, overshoot, steady state).

While a variety of relief valves may be used with the invention, one particular form of force balanced valve utilized as exhalation valves has been shown to be advantageous. FIG. 3 illustrates two types of such exhalation valves, which are of the balloon or diaphragm type. The balloon type valve illustrated in FIG. 3(a) incorporates a balloon 30 inflated by pressure from pilot pressure inlet 32, the expiratory flow will open the valve when the expiratory flow force on the valve exceeds the force created from the pilot pressure.

Figure 3B:
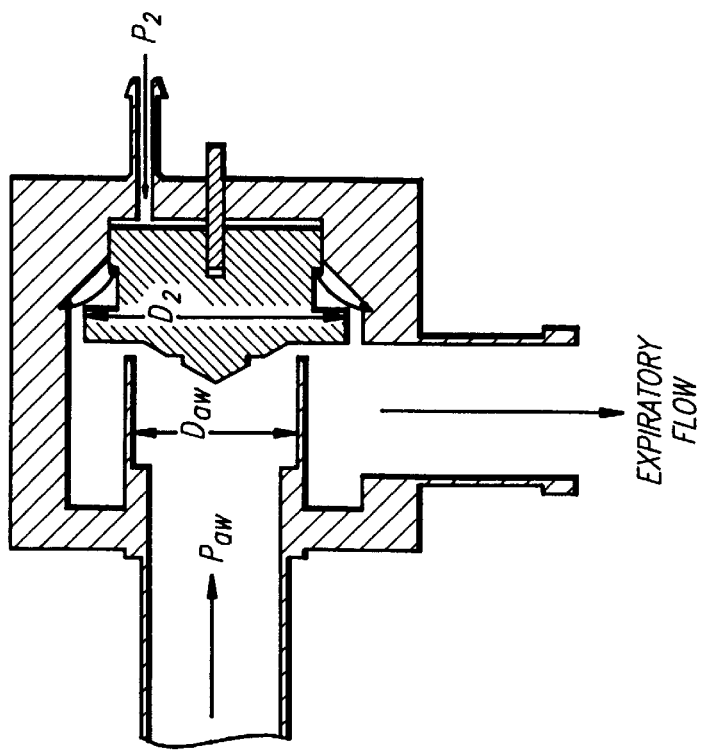
FIGS. 3(a) and 3(b) illustrate two examples of typical force balance valves.
Figure 3A:
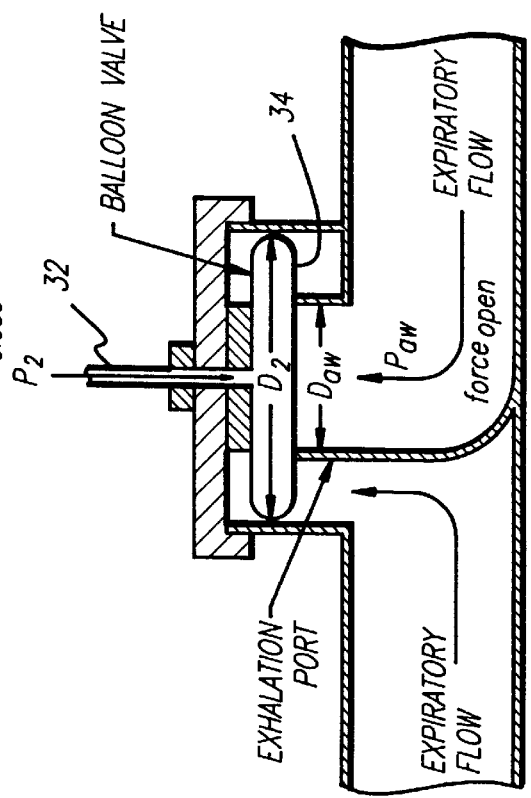

Similarly, the diaphragm valve of FIG. 3(b) is provided with pilot pressure inlet 32 operating on the cavity formed by the valve exterior body, the valve poppet and the area behind diaphragm 34, thus controlling expiratory flow similarly to balloon valve 3(a). While it has been shown that such valves are useful for the purposes of the relief valve of the invention, other valves which are electrically, mechanically or pneumatically driven, or a combination of these drive schemes, can be advantageously utilized for the relief valve of the invention.

From the foregoing, it should be clear that the invention provides for an improved pneumatically driven, electronically controlled, pressure control system for a ventilator system for providing breathing gas to a patient at a desired flow rate and pressure level. More particularly, the invention allows elimination of longterm overshoot as well as minimization of transient overshoot of patient airway pressure above the target set by a care provider by allowing for the incorporation of target flow trajectories of more sophisticated ventilation strategies.

Figure 5A:
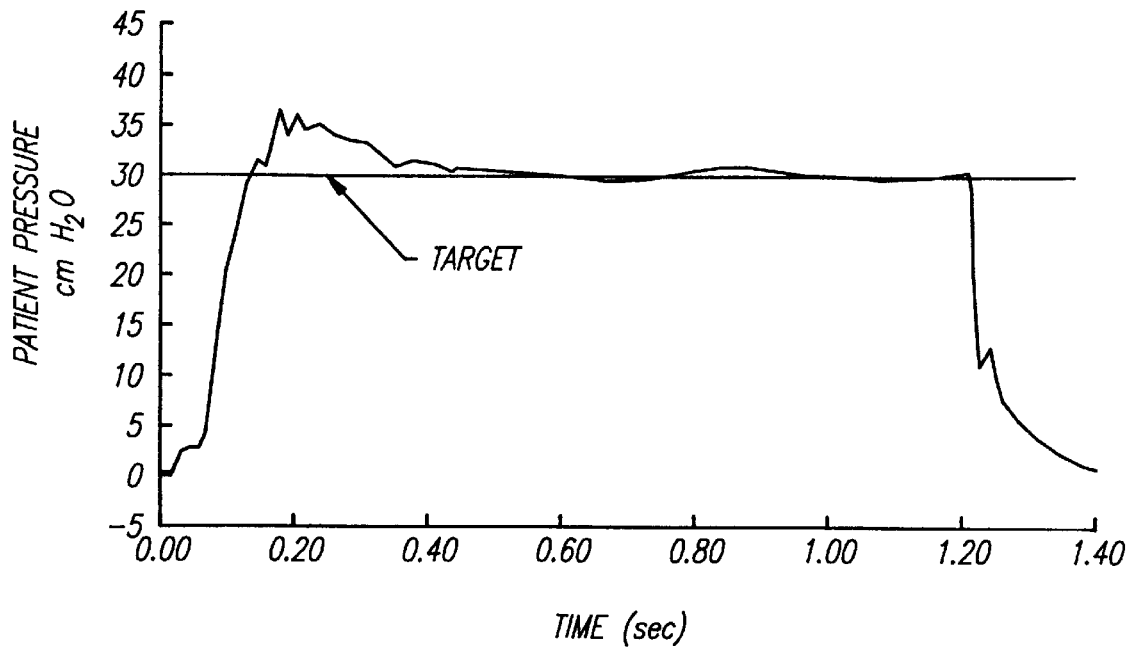
FIGS. 5(a) and 5(b) illustrate a pressure controlled inspiration phase using the control system of the invention.
Figure 5B:
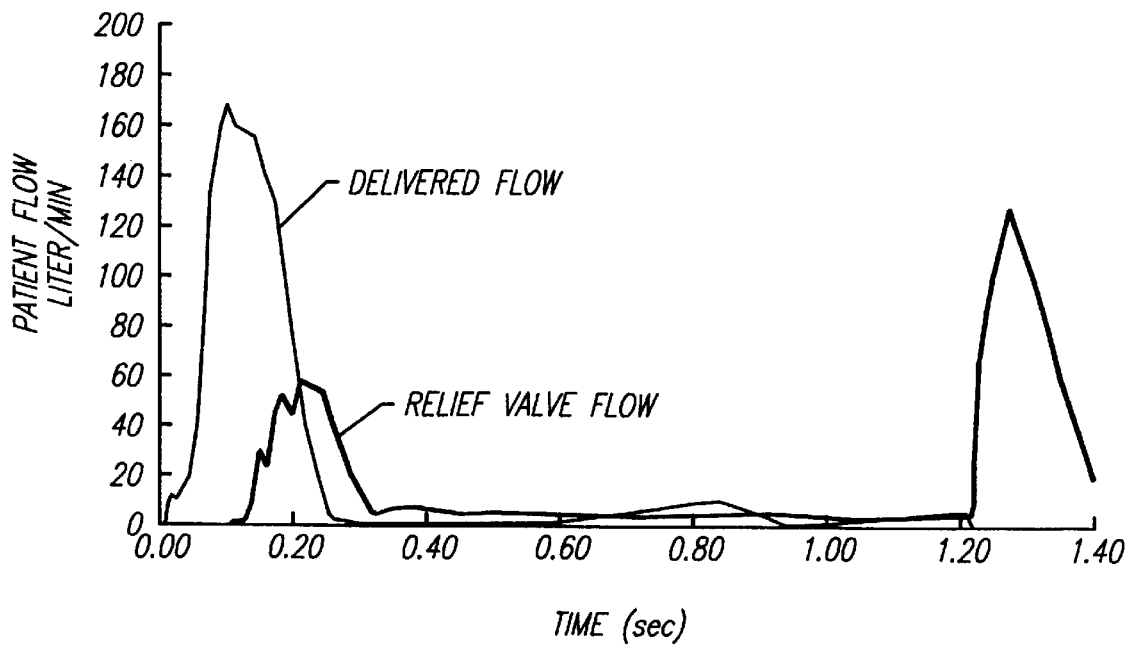

FIG. 5 illustrates the improved performance of a system utilizing the control system of the present invention. Referring to FIG. 5(a), a rapid rise time is utilized, as shown in FIG. 4(a), to facilitate rapid filling of the lungs of the patient once a breath is begun. Unlike the prior art controllers, however, the present invention is able to eliminate short term overshoot of pressure by providing a preinspiratory flow of breathing gas through the relief valve in the exhalation flow path, and is able to eliminate the sustained overshoot of pressure after lung filling, so that airway pressure can be maintained at the desired pressure such as about 30 cm $H_2O$. Referring to FIG. 5(b), the time history of flow rate flow to the patient is illustrated, as is the flow from the relief valve. It can be seen that the actively controlled flow rates from the relief valve near the early peaking of pressure can allow rapid return of patient airway pressure to the desired level. Additionally, as shown by the graph at the 1.2 second mark, the relief valve can be used to rapidly reduce pressure in the airway for the beginning of the expiration cycle. Thus, the use of the invention substantially reduces the sustained overpressure of the patent when compared to prior art controllers.

It should be recognized that although the invention has been described as providing individual, separate pressure, flow, and exhalation controllers, it is also possible that these functions can be performed by one or more microprocessors with appropriate inputs from the flow and pressure sensors provided, and outputs to the supply flow valve and pressure regulator mechanism.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method of controlling airway pressure in a ventilator for a patient during the inspiratory cycle of a breath, the breathing gas circuit having a source of breathing gas, an airway flow path supplying the breathing gas to a breathing attachment for the patient, a flow supply valve for controlling the supply of breathing gas to the breathing attachment for the patient, a relief valve for controlling venting of breathing gas from the patient to the atmosphere, the airway flow path being in fluid communication with the breathing attachment for the patient, the steps of the method comprising:

delivering a supply flow of breathing gas to the patient breathing attachment through the flow supply valve at a predetermined rate of supply flow based upon a desired airway pressure and actual airway pressure;

determining a desired rate of outflow through the relief valve;

generating a relief valve command signal based upon the airway pressure and the desired rate of outflow to control operation of the relief valve to vent the breathing gas from the relief valve; and venting the breathing gas from the patient breathing attachment through the relief valve during the inspiratory cycle at a rate based upon the airway pressure and the desired rate of outflow.

2. The method of claim 1, further including the steps of determining the predetermined rate of supply flow based upon the desired airway pressure and actual airway pressure, and generating a supply valve command signal to control operation of the flow supply valve to deliver the breathing gas at the predetermined rate of supply flow.

3. The method of claim 2, further including the steps of measuring the actual rate of supply flow from the flow supply valve to the breathing attachment, comparing the actual rate of supply flow with the predetermined rate of supply flow to determine a supply flow error, and modifying the supply valve command signal based upon the supply flow error.

4. The method of claim 2, further including the steps of measuring the actual airway pressure, comparing the actual airway pressure with the instantaneous desired airway pressure to determine an airway pressure error, and modifying the desired rate of flow based upon the airway pressure error.

5. The method of claim 1, further including the steps of measuring the actual rate of outflow through the relief valve, comparing the actual rate of outflow with the desired rate of outflow to determine an outflow error, and modifying the relief valve command signal based upon the outflow error.

6. The method of claim 1 wherein the relief valve comprises an exhalation valve for controlling the venting of breathing gas and exhaled gas in the patient's airway.

7. A system for closed loop control of airway pressure during the inspiratory cycle of a ventilator having a breathing gas circuit for a patient, a source of breathing gas in the breathing gas circuit, and an airway flow path supplying the breathing gas to a breathing attachment for the patient, the system comprising:

flow supply valve means in said airway flow path for delivering a supply flow of breathing gas from the source of breathing gas to the breathing attachment for the patient at a desired rate of supply flow based upon a desired airway pressure and the actual airway pressure;

a relief valve for venting breathing gas from the patient breathing attachment to the atmosphere during the inspiratory cycle at a desired rate of outflow based upon a desired rate of outflow and the airway pressure to achieve the desired airway pressure;

means for determining the desired rate of outflow from said relief valve; and means for generating a relief valve command signal to control operation of said relief valve to vent the breathing gas at the desired rate of outflow.

8. The system of claim 7, further including means for determining the desired rate of supply flow based upon the instantaneous desired airway pressure and the actual airway pressure, and means for generating a supply valve command signal to control operation of the flow supply valve means to deliver the breathing gas at the desired rate of supply flow.

9. The system of claim 8, further including means for measuring the actual rate of supply flow from the flow supply valve means to the breathing attachment, means for comparing the actual rate of supply flow with the desired rate of supply flow to determine a supply flow error, and means for modifying the supply valve command signal based upon the supply flow error.

10. The system of claim 8, further including means for measuring the actual airway pressure, means for comparing the actual airway pressure with the desired airway pressure to determine an airway pressure error, and means for modifying the desired rate of flow based upon the airway pressure error.

11. The system of claim 8, wherein said relief valve further comprises an exhalation valve which is attached to said patient breathing attachment for venting breathing gas and exhaled breathing gas.

12. The system of claim 7, further including means for measuring the actual rate of outflow through the exhalation valve means, means for comparing the actual rate of outflow with the desired rate of outflow to determine an outflow error, and means for modifying the exhalation valve command signal based upon the outflow error.

13. An apparatus for the control of patient airway pressure in a ventilation respirator which comprises:

means to set a desired target airway pressure;

a pressure controller;

a flow valve controller;

a breathing gas flow valve;

a sensor for measuring the output flow of breathing gas from said breathing gas flow valve;

a patient tubing airway system in fluid communication with said flow valve and the patient respiratory system;

a pressure sensor in fluid communication with said patient airway system;

first summing means to create an error signal between the predetermined airway pressure and a signal from the pressure sensor, said error signal providing the signal to drive the pressure controller;

second summing means to determine the error between the output signal from the flow controller and the patient airway flow sensor output signal, said error signal providing an input to said flow valve controller;

a relief valve in fluid communication with said patient airway system and having a flow outlet;

a relief valve flow sensor in fluid communication with the flow outlet of said relief valve for measuring relief valve flow;

third summing means which outputs a desired relief flow error signal based upon the difference between a desired relief flow and the relief valve flow measured by the relief valve flow sensor; and a relief valve controller which outputs a command signal to said relief valve to vent flow during inspiration based upon the signal from the pressure sensor and the desired relief flow error signal.

14. The apparatus of claim 13 wherein said relief valve is an actively controlled relief valve.

15. The apparatus of claim 14 wherein the desired relief flow is a function of airway pressure.

* * * * *